United States Patent [19]

Maurer

[11] Patent Number: 4,703,122
[45] Date of Patent: Oct. 27, 1987

[54] PROCESS FOR PREPARING O-PYRIMIDINYL N,N-DIMETHYL-CARBAMATES

[75] Inventor: Fritz Maurer, Wuppertal, Fed. Rep. of Germany

[73] Assignee: Bayer Aktiengesellschaft, Leverkusen, Fed. Rep. of Germany

[21] Appl. No.: 778,342

[22] Filed: Sep. 20, 1985

[30] Foreign Application Priority Data

Oct. 5, 1984 [DE] Fed. Rep. of Germany ....... 3436478

[51] Int. Cl.$^4$ ........................................... C07D 239/34
[52] U.S. Cl. ..................................... 544/319; 544/253
[58] Field of Search ................ 544/253, 287, 319, 352

[56] References Cited

U.S. PATENT DOCUMENTS 4,323,571  4/1982  Maurer et al. ....................... 544/319
4,352,806 10/1982  Katz et al. ............................ 544/319
4,503,057  3/1985  Maurer et al. ....................... 544/319

FOREIGN PATENT DOCUMENTS 3211035  9/1983  Fed. Rep. of Germany ...... 544/319

Primary Examiner—Henry R. Jiles
Assistant Examiner—J. G. Mullins
Attorney, Agent, or Firm—Sprung Horn Kramer & Woods

[57] ABSTRACT

The invention relates to a new process for preparing O-pyrimidinyl N,N-dimethylcarbamates of the formula (I)

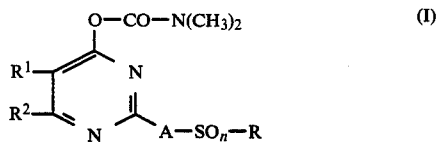

in which
R stands for straight-chain or branched alkyl,
R$^1$ stands for hydrogen or optionally substituted radicals from the series alkyl, alkoxy, alkylthio, alkylsulphinyl or alkylsulphonyl,
R$^2$ stands for hydrogen or optionally substituted alkyl or
R$^1$ and R$^2$ together can form a fused-on optionally substituted saturated or unsaturated ring,
A stands for straight-chain or branched alkylene and
n stands for 0, 1 or 2.

Components of the above formula (I) are obtained when hydroxypyrimidines of the formula (II)

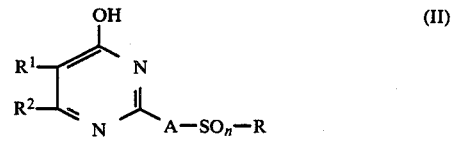

in which
R, R$^1$, R$^2$, A and n have the above mentioned meanings, are reacted with N,N-dimethylcarbamoyl halides of the formula (III)

$$\text{Hal—CO—N(CH}_3\text{)}_2 \quad \text{(III)}$$

in which
Hal stands for chlorine or bromine, at temperatures between 0° C. and 150° C. and in particular between 20° C. and 100° C. in the presence of a catalytic amounts of a bicyclic organic amine, in the presence of acid acceptors and in the presence of a diluent.

The bicyclic organic amines are preferably 1,4-diazabicyclo(2,2,2)-octane (DABCO) and quinuclidine, DABCO being particularly preferable. The O-pyrimidinyl N,N-dimethylcarbamates of formula (I) are highly active insecticides.

11 Claims, No Drawings

PROCESS FOR PREPARING O-PYRIMIDINYL N,N-DIMETHYL-CARBAMATES

The invention relates to a new process for preparing O-pyrimidinyl N,N-dimethylcarbamates from hydroxypyrimidines in the presence of a bicyclic amine as a catalyst.

It is already known that O-pyrimidinyl N,N-dimethylcarbamates are obtained when hydroxypyrimidines are reacted with N,N-dimethylcarbamoyl halides in the presence of inorganic bases, such as, for example, sodium carbonate or potassium carbonate (cf. DE-OS [German Published Specification] No. 2,928,185.

The disadvantages of this process are that very long residence times are necessary, that large amounts of isomeric by-products are formed, and that the yields are as a result frequently very unsatisfactory.

According to DE-OS [German Published Specification] No. 3,211,035 (process variant (a)) the process for preparing O-pyrimidinyl-N,N-dimethylcarbamates from hydroxypyrimidines and N,N-dimethylcarbamoyl halides in the presence of diazabicyclooctane, diazabicyclononane and diazabicycloundecane as acid acceptors seems to be possible. As to this compare with page 32, last paragraph of the above called DE-OS.

In DE-OS No. 3,211,035 the use of catalytic amounts of a bicyclic organic amine (preferably of 1,4-diazabicyclo-(2,2,2)-octane) in the presence of acid acceptors is neither disclosed nor rendered obvious.

It has now been found that O-pyrimidinyl N,N-dimethylcarbamates of the formula (I)

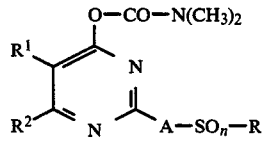

in which
R stands for straight-chain or branched alkyl,
$R^1$ stands for hydrogen or optionally substituted radicals from the series alkyl, alkoxy, alkylthio, alkylsulphinyl or alkylsulphonyl,
$R^2$ stands for hydrogen or optionally substituted alkyl or
$R^1$ and $R^2$ together can form a fused-on optionally substituted saturated or unsaturated ring,
A stands for straight-chain or branched alkylene and
n stands for 0, 1 or 2,
are obtained
when hydroxypyrimidines of the formula (II)

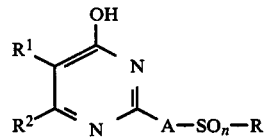

in which R, $R^1$, $R^2$, A and n have the abovementioned meanings, are reacted with N,N-dimethylcarbamoyl halides of the formula (III)

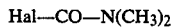

in which

Hal stands for chlorine or bromine, at temperatures between 0° C. and 150° C. and in particular between 20° C. and 100° C. in the presence of catalytic amounts of a bicyclic organic amine, in the presence of acid acceptors and in the presence of a diluent.

The bicyclic organic amines are preferably 1,4-diazabicyclo-(2,2,2)-octane (DABCO) and quinuclidine, DABCO being particularly preferable. The bicyclic organic amine is used in catalytic amounts.

It is possible, surprisingly, to use the process according to the invention to carry out the reaction with very short residence times, in high yield and purity. This is all the more surprising since, from the state of the art, the formation of isomeric by-products should have been expected to take place to a considerable extent.

The process according to the invention is preferably used to prepare the following compounds of the formula (I) in which
R stands for straight-chain or branched alkyl having 1 to 6 carbon atoms, in particular 1 to 4 carbon atoms,
$R^1$ stands for hydrogen or for alkyl, alkoxy or alkylthio, alkylsulphinyl or alkylsulphonyl, each having 1 to 6 carbon atoms, in particular 1 to 4 carbon atoms, which can be optionally substituted by halogen or $C_1$–$C_2$-alkoxy,
$R^2$ stands for hydrogen or alkyl having 1 to 6 carbon atoms, in particular 1 to 4 carbon atoms, which can be optionally substituted by halogen, in particular chlorine or fluorine, or $C_1$–$C_2$-alkoxy, or
$R^1$ and $R^2$ together can stand for alkylene having 2 to 4 carbon atoms which can be optionally substituted by halogen, in particular chlorine or fluorine, or $C_1$–$C_2$-alkyl,
A stands for straight-chain or branched alkylene having 1 to 6 carbon atoms, in particular 1 to 4 carbon atoms, and
n stands for 0, 1 or 2.

If, for example, 4-hydroxy-5-methoxy-2-methylthiomethylpyrimidine and N,N-dimethylcarbamoyl chloride are used as starting materials for the process according to the invention in the presence of catalytic amounts of 1,4-diazabicyclo-(2,2,2)-octane (DABCO), the reaction can be represented by the following formula diagram:

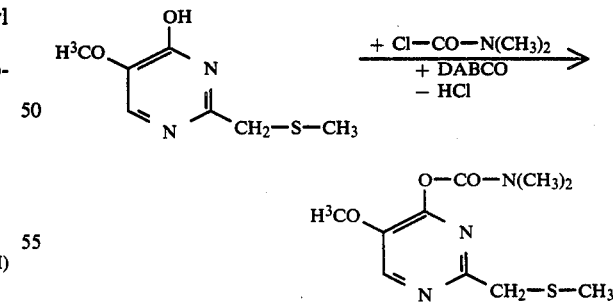

The hydroxypyrimidines to be used as starting materials for carrying out the process according to the invention are defined in general by the formula (II). In said formula, R, $R^1$, $R^2$, A and n preferably stand for those radicals and indices which have been mentioned as preferred in the definition of R, $R^1$, $R^2$, A and n in the formula (I).

The compounds of the formula (II) are known and/or can be prepared by methods known per se (cf. DE-OS [German Published Specification] No. 2,838,359, DE-OS [German Published Specification] No. 2,928,185 and DE-OS [German Published Specification] No. 3,211,035).

The compounds of the formula (III) are known compounds of organic chemistry. An example which may be mentioned is N,N-dimethylcarbamoyl chloride.

The process for preparing O-pyrimidinyl N,N-dimethylcarbamates in accordance with the invention is generally carried out using diluents. These can be virtually any inert organic solvent, including in particular aliphatic and aromatic, optionally chlorinated hydrocarbons, such as petrol, benzene, toluene, xylene, methylene chloride, chloroform, carbon tetrachloride, chlorobenzene and o-dichlorobenzene, ethers such as diethyl ether and dibutyl ether, tetrahydrofuran and dioxane, ketones such as acetone, methyl ethyl ketone, methyl isopropyl ketone and methyl isobutyl ketone and nitriles such as acetonitrile and propionitrile.

The process according to the invention is carried out using acid acceptors. The acid acceptors which find utility can be any customary acid-binding agents. Those which have been found to be particularly useful are alkali metal carbonates, such as sodium carbonate and potassium carbonate, and aliphatic, aromatic or heterocyclic amines, for example triethylamine, trimethylamine, dimethylaniline, dimethylbenzylamine and pyrimidine.

The process according to the invention is carried out in the presence of a bicyclic organic amine and in particular in the presence of 1,4-diazabicyclo-(2,2,2)-octane (DABCO) as a catalyst.

In a preferred embodiment, the acid acceptors used are alkali metal carbonates, in particular Na$_2$CO$_3$ and/or K$_2$CO$_3$, and catalytic amounts of DABCO.

The process according to the invention is generally carried out at temperatures between 0° C. and 150° C. Preference is given to the temperature range between 20° C. and 100° C. The reactions are generally carried out under atmospheric pressure.

To carry out the process according to the invention, 1.0 to 1.3 mol, preferably between 1.0 and 1.2 mol, of N,N-dimethylcarbamoyl chloride and 0.01 to 0.08 mol, preferably between 0.02 to 0.06 mol, of bicyclic organic amine, in particular DABCO, are used per mol of hydroxypyrimidine of the formula (II). The reaction is carried out in a diluent in the presence of an acid acceptor. After the reaction has taken place, the reaction product is filtered and the solvent is distilled off in vacuo.

The compounds of the formula (I) are as a rule obtained in solid form and can be purified by recrystallization. They are characterised on the basis of the melting point.

The O-pyrimidinyl N,N-dimethylcarbamates prepared using the process according to the invention are highly active insecticides (cf. DE-OS [German Published Specification] No. 2,928,185 and DE-OS [German Published Specification] No. 3,211,035).

PREPARATION EXAMPLES

Example 1

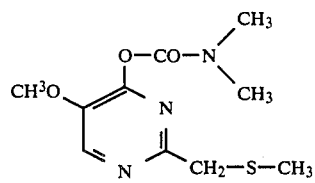

11.65 g (0.103 mol) of 95% N,N-dimethylcarbamidic acid chloride are added to a mixture of 19.5 g (0.1 mol) of 95.2% 2-methylthiomethyl-4-hydroxy-5-methoxypyrimidine, 100 ml of chloroform, 13.2 g (0.125 mol) of anhydrous sodium carbonate and 0.56 g (0.005 mol) of diazabicyclo(2,2,2)-octane. The temperature of the reaction mixture rises to about 34° C. and then slowly drops back. After 1½ hours no precursor is present any longer. The inorganic salt is filtered off with suction and is washed with chloroform, and the solvent is subsequently removed in vacuo.

The result obtained is 27.3 g of 93% strength O-(2-methylthiomethyl-5-methoxypyrimidin-4-yl) N,N-dimethylcarbamate (99% of theory) in the form of beige crystals having a melting point of 96° C.

The same method is used to obtain for example the following compound:

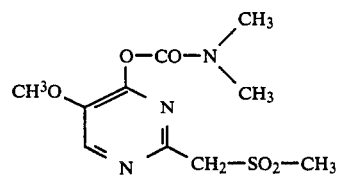

Yield: 99% of theory.
Melting point: 118° C.

Comparative example from DE-OS [German Published Specification] No. 2,928,185

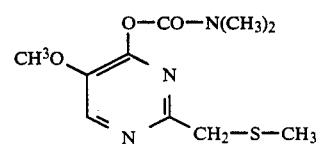

A mixture of 18.6 g (0.1 mol) of 2-methylthiomethyl-4-hydroxy-5-methoxypyrimidine, 16.6 g (0.12 mol) of potassium carbonate, 200 ml of acetonitrile and 10.8 g (0.1 mol) of dimethylcarbamoyl chloride is refluxed for 7 hours, is cooled down to room temperature and is then filtered. The filtrate is evaporated in vacuo.

The result obtained is 19.5 g (76% of theory) of O-(2-methylthiomethyl-5-methoxypyrimidin-4-yl) N,N-dimethylcarbamate in the form of beige crystals having a melting point of 97° C.

What is claimed is:

1. A process for preparing an O-pyrimidinyl N,N-dimethylcarbamate of the formula

[Structure: pyrimidine ring with R¹ at 5-position, R² at 6-position (via CH), O-CO-N(CH₃)₂ at 4-position, and A-SO$_n$-R at 2-position]

in which

R stands for straight-chain or branched alkyl having 1 to 6 carbon atoms,

R$^1$ stands for hydrogen or for alkyl, alkoxy or alkylthio, alkylsulphinyl or alkylsulphonyl, each having 1 to 6 carbon atoms which can be optionally substituted by halogen or C$_1$-C$_2$-alkoxy, R$^2$ stands for hydrogen or alkyl having 1 to 6 carbon atoms which can be optionally substituted by halogen, or C$_1$-C$_2$-alkoxy, or R$^1$ and R$^2$ together can stand for alkylene having 2 to 4 carbon atoms which can be optionally substituted by halogen or C$_1$-C$_2$-alkyl, A stands for straight-chain or branched alkylene having 1 to 6 carbon atoms and n stands for 0, 1 or 2, comprising reacting a hydroxypyrimidine of the formula

[Structure: pyrimidine ring with R¹, R², OH and A-SO$_n$-R substituents]

in which

R, R$^1$, R$^2$, A and n have the abovementioned meanings, with an N,N-dimethylcarbamoyl halide of the formula Hal—CO—N(CH$_3$)$_2$ in which Hal stands for chlorine or bromine, in the presence of an acid acceptor selected from the group consisting of an alkali metal carbonate, triethylamine, trimethylamine, dimethylaniline, dimethylbenzylamine and pyrimidine and in the presence of 0.01 to 0.08 times the molar amount of a bicyclic organic amine based on the hydroxypyrimidine and in the presence of a diluent.

2. A process according to claim 1, wherein the reaction is carried out at temperatures between 0° C. and 150° C.

3. A process according to claim 1, wherein the reaction is carried out at temperatures between 20° C. and 100° C.

4. A process according to claim 1, wherein the bicyclic organic amine used is 1,4-diazabicyclo-(2,2,2)-octane.

5. A process according to claim 1 in which

R stands for straight-chain or branched alkyl having 1 to 4 atoms,

R$^1$ stands for hydrogen or for alkyl, alkoxy or alkylthio, alkylsulphinyl or alkylsuphonyl, each having 1 to 4 carbon atoms, which can be optionally substituted by halogen or C$_1$-C$_2$-alkoxy, R$^2$ stands for hydrogen or alkyl having 1 to 4 carbon atoms, which can be optionally substituted by halogen, or C$_1$-C$_2$-alkoxy, or R$^1$ and R$^2$ together can stand for alkylene having 2 to 4 carbon atoms which can be optionally substituted by halogen, or C$_1$-C$_2$-alkyl, A stands for straight-chain or branched alkylene having 1 to 4 carbon atoms, and n stands for 0, 1 or 2.

6. A process according to claim 1 for preparing O-(2-methylthiomethyl-5-methoxypyrimidin-4-yl) N,N-dimethylcarbamate.

7. A process according to claim 1, wherein 1.0 to 1.3 mol of N,N-dimethylcarbamoyl chloride and 0.01 to 0.08 mol of 1,4-diazabicyclo-(2,2,2)-octane are used per mol of hydroxypyrimidine.

8. A process according to claim 1, wherein 1.0 to 1.2 mol of N,N-dimethylcarbamoyl chloride and 0.02 to 0.06 mol of 1,4-diazabicyclo-(2,2,2)-octane are used per mol of hydroxypyrimidine.

9. A process according to claim 1, wherein the diluent is an inert organic solvent.

10. A process according to claim 1, in which halogen is chlorine or fluorine.

11. A process according to claim 5, wherein halogen is chlorine or fluorine.

* * * * *